United States Patent [19]

Schmidt et al.

[11] Patent Number: 5,618,824
[45] Date of Patent: Apr. 8, 1997

[54] TREATMENT OF OBSESSIVE-COMPULSIVE DISORDERS WITH 5-HT$_2$ ANTAGONISTS

[75] Inventors: Christopher J. Schmidt, Oregonia; John H. Kehne, Cincinnati; Robert A. Padich, Mason, all of Ohio

[73] Assignee: Merrell Pharmaceuticals Inc., Cincinnati, Ohio

[21] Appl. No.: 209,084

[22] Filed: Mar. 9, 1994

[51] Int. Cl.$^6$ ................................................ A61K 31/445
[52] U.S. Cl. .......................................... 514/317; 514/331
[58] Field of Search ..................................... 514/317, 331

[56] References Cited

U.S. PATENT DOCUMENTS

| | | | |
|---|---|---|---|
| 4,783,471 | 11/1988 | Carr et al. | 514/317 |
| 5,288,749 | 2/1994 | Meyer et al. | 514/414 |
| 5,296,491 | 3/1994 | Shutske et al. | 514/303 |
| 5,326,768 | 7/1994 | van Wijngaarden et al. | 514/292 |
| 5,441,961 | 8/1995 | Cohen et al. | 514/288 |

FOREIGN PATENT DOCUMENTS

| | | |
|---|---|---|
| 0319962 | 6/1989 | European Pat. Off. . |
| 0337136 | 10/1989 | European Pat. Off. . |
| 9414801 | 7/1994 | WIPO . |
| 9500131 | 1/1995 | WIPO . |
| 9501976 | 1/1995 | WIPO . |

OTHER PUBLICATIONS

Lucey, J.V. et al., Int. Clin. Psychopharmacol., vol. 7, No. 1, 1992–pp. 45–49.

Sorenson, S.M. et al., J. Pharmacol. Exp. Ther., vol. 266, No. 2, Aug. 1993, pp. 684–691.

Schreiber et al., Eur. J. Pharmacol., vol. 264, No. 1, 13 Oct. 1994.

Swerdlow, Neal R. Behavioral and Brain Sciences, (1987) 10, 197–245.

Baxter, Lewis R. Jr. et al., Arch Gen Physhiatry, vol. 44, Mar. 1987, pp. 211–218.

Rapoport, Judith L. M.D. et al., Phychopharmacology Bulletin, vol. 24, No. 3, 1988, pp. 380–384.

Bastani Bijan et al., Arch Gen Physhiatry, vol. 47, Sep. 1990. pp. 833–839.

Benkelfat, Chawki et al., Arch Gen Physhiatry, vol. 47, Sep. 1990. pp. 840–848.

Swerdlow, N.R. et al., Psychopharmacology, (1992) 108: 189–195.

Swerdlow N.R. et al., Journal of Psychopharmacology, 6(2) (1992) 176–190.

Swerdlow, N.R. et al., Biol Psychiatry, 1993, 33: pp. 298–301.

Kehne, John H. et al., The Journal of Pharmacology and Experimental Therapeutics, vol. 260, No. 1, pp. 78–89, 1990.

Murphy, David M.D., Neuropsychopharmacology, 1990, vol. 3, No. 56, pp. 457–471.

Padich, Robert A., "Text Related to Serotonin and Obsessive Compulsive Disorder" Abstract of Dissertation on file with the Un. of Cincinnati (Summer 1993).

Primary Examiner—Marianne M. Cintins
Assistant Examiner—William R.A. Jarvis
Attorney, Agent, or Firm—Michael J. Sayles

[57] ABSTRACT

The present invention is directed to 5-HT$_2$ antagonists and their use as agents in the treatment of obsessive-compulsive disorders (OCD). The invention is particularly directed to the compound (+)-α-(2,3-dimethoxyphenyl)-1-[2-(4-fluorophenyl)ethyl]-4-piperidinemethanol which is a member of a class of 5-HT$_2$ antagonists known as N-aralkyl piperidinemethanol derivatives which are potent and selective inhibitors of the binding of serotonin at the 5-HT$_2$ receptor site.

3 Claims, 1 Drawing Sheet

TREATMENT OF OBSESSIVE-COMPULSIVE DISORDERS WITH 5-HT$_2$ ANTAGONISTS

The present invention is directed to the use of 5-HT$_2$ antagonists as agents in the treatment of obsessive-compulsive disorders (OCD).

BACKGROUND OF THE INVENTION

Clinical studies of 5-HT subtype-selective agonists or antagonists have suggested a role of 5-HT in the etiology and treatment of such different neuropsychiatric disorders as the anxiety disorders, depression, alcoholism, schizophrenia, migraine, sexual dysfunctions and Alzheimer's disease (see Murphy, D., *Neuropsychiatric Disorders and the Multiple Human Brain Serotonin Receptor Subtypes and Subsystems*, Neuropsychopharmacology, 3, No. 5/6, pp. 457–471 (1990). Pharmacological and clinical data suggest that 5-HT and in particular 5-HT$_2$ receptors may play a role in schizophrenic symptomology and in the mechanism of action of some antipsychotic drugs.

A phenomenon known as prepulse inhibition (PPI) is known to be disrupted in individuals with schizophrenia. PPI is a measure of "sensory gating" or "sensory filtering" in animals and man and disrupted PPI may represent a fundamental deficit in the ability of these individuals to gate sensory information. Studies have shown that the amplitude of the startle reflex is inhibited when the startling stimulus is preceded 30–500 msec by a weak "prepulse". This "prepulse inhibition" (PPI) is a measure of sensorimotor gating that is impaired in disorders characterized by deficient gating of irrelevant sensory information (schizophrenia) or motor activity (Huntington's Disease). Substantial evidence indicates that PPI is modulated by neural circuitry linking the limbic cortex, striatum and pallidum.

It has recently been demonstrated that patients with obsessive-compulsive disorders (OCD) also fail to inhibit or "gate" intrusive, distressing thoughts or images. Since OCD is characterized by deficient "cognitive gating" and by aberrant metabolic activity in circuitry linking the orbital cortex and striatum, it has been predicted that OCD patients might exhibit deficient PPI. Indeed, in a study of eleven OCD patients and 13 normal controls, it was demonstrated that OCD patients exhibited less PPI than control subjects. Swerdlow, N. R., Benbow, C. H., Zisook, S., Geyer, M. A., and Braff, D. L., *Impaired Sensorimotor Gating in Obsessive Compulsive Disorder*(OCD), abstract from the *Abstracts of Panels and Posters*, p. 155, American College of Neuropsychopharmacology 31st Annual Meeting, San Juan, Puerto Rico, Dec. 14–18, 1992. These findings suggest that the inability to "gate" intrusive thoughts and images in OCD is accompanied by quantifiable deficits in sensorimotor gating and suggests PPI might be a useful measure for understanding the pathophysiology of OCD. Currently, serotonin-selective reuptake inhibitors (SSRI) are used to treat the symptoms of OCD. However, we are not aware of any data, other than such data as is presented herein, that indicates that SSRIs reverse the deficits in PPI in OCD.

SUMMARY OF THE INVENTION

We have found that pharmacological agents that increase serotonergic activity (i.e. 5-HT releasing agents such as fenfluramine) disrupt sound-induced PPI in rats. This suggests a model for studying the restoration of PPI in subjects where PPI has been disrupted by such agents. We now show that the (+)-isomer of α(2,3-dimethoxyphenyl)-1-[2-(4-fluorophenyl)ethyl]-4-piperidinemethanol, a serotonin 5-HT$_2$ antagonist which possesses superior in vivo potency, is active in a model of sensory-motor gating (prepulse inhibition) disrupted by 5-HT$_2$ receptor activation and restores sound-induced PPI that is disrupted by fenfluramine. This compound can be described by the following formula I:

Formula I

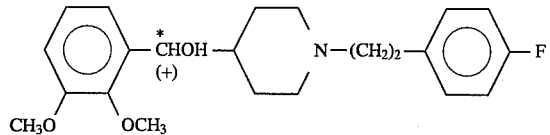

This is the first known instance that we are aware of where it has been demonstrated that a 5-HT$_2$ antagonist can restore disrupted prepulse inhibition. We have also shown that (+)-α-(2,3-dimethoxyphenyl)-1-[2-(4-fluorophenyl)ethyl]-4-piperidinemethanol specifically restores sound-disrupted prepulse inhibition and not light-disrupted prepulse inhibition which may have further implications for the treatment of OCD. This activity demonstrates that the 5-HT$_2$ antagonist α-(2,3-dimethoxyphenyl)-1-[2-(4-fluorophenyl)ethyl]-4-piperidine-methanol would be useful in the treatment of OCD disorders and suggests that 5-HT$_2$ antagonists in general would be useful for this purpose. The compound, α-(2,3-dimethoxyphenyl)-1-[2-(4-fluorophenyl)ethyl]-4-piperidinemethanol, belongs to a class of compounds known as N-aralkyl piperidinemethanol derivatives which are potent and selective inhibitors of the binding of serotonin at the 5-HT$_2$ receptor site. These compounds are represented by formula II:

Formula II

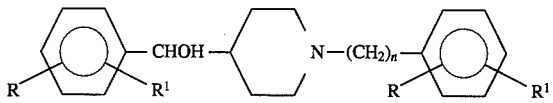

wherein n is 2, 3 or 4 and each R and R$^1$ independently represents hydrogen, C$_{1-6}$ alkyl, halogen, trifluoromethyl, hydroxy, C$_{1-6}$ alkoxy, or amino, their optical isomers and mixtures thereof and the pharmaceutically acceptable salts thereof. These N-aralkyl piperidinemethanol derivatives as well as the processes for their preparation are described in detail in U.S. Pat. Nos. 4,783,471, 4,912,117, and 5,169,096 incorporated herein by reference.

BRIEF DESCRIPTION OF THE DRAWINGS

FIG. 1a shows the 5-HT/DA releaser MDMA (3,4-mehtylenedioxymethamphetamine) blocks prepulse inhibition in rats, using either a sound or light prepulse.

FIG. 1b shows that MDL, but not haloperidol, reduces the MDMA blockade of sound prepulse inhibition.

DETAILED DESCRIPTION OF THE INVENTION

Figure 1A:
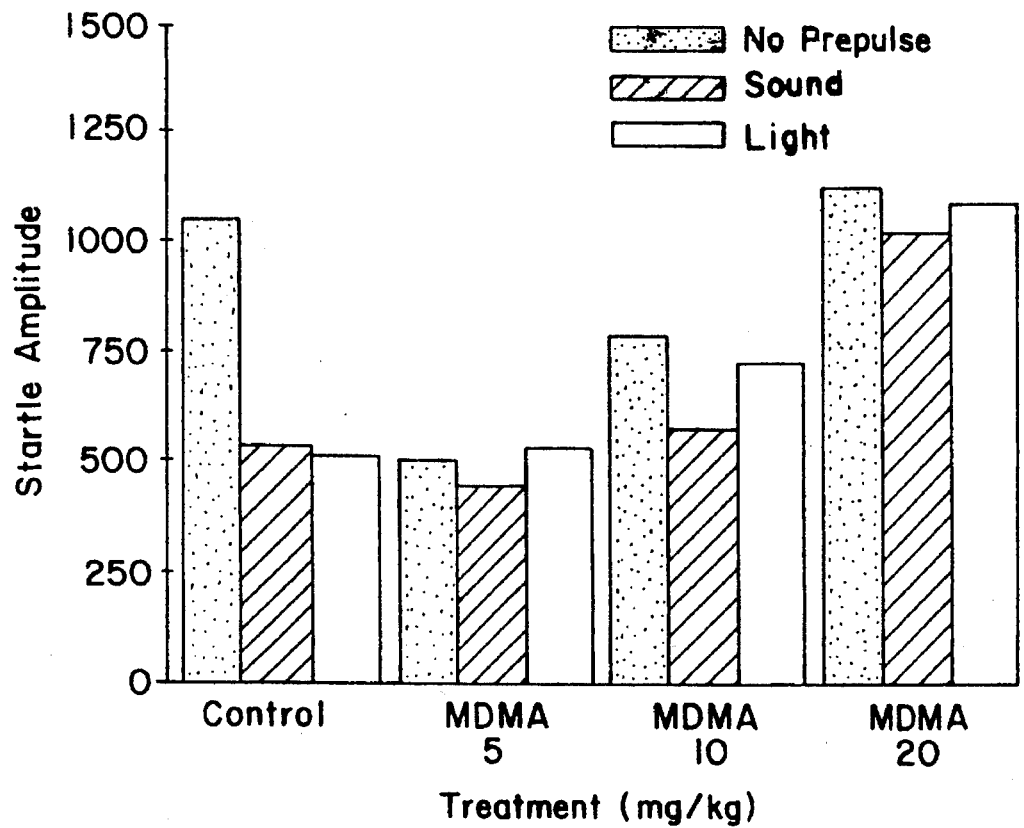
FIGS. 1a–1b demonstrate that (+)-α-(2,3-dimethoxyphenyl)-1-[2-(4-fluorophenyl)ethyl]-4-piperidinemethanol (MDL) reverses deficits in sensorimotor gating (prepulse inhibition) produced by 5-HT$_2$ receptor acivation.

The compound (+)-α-(2,3-dimethoxyphenyl)-1-[2-(4-fluorophenyl)ethyl]-4-piperidinemethanol is a potent and selective antagonist of 5-HT$_2$ receptors. The 5-HT$_2$ antagonist activity of (+)-α-(2,3-dimethoxyphenyl)-1-[2-(4-fluorophenyl)ethyl]-4-piperidinemethanol is demonstrated and described in detail in U.S. Pat. No. 5,134,149 which is incorporated herein by reference.

We have now evaluated its activity in a model of sensory-motor gating (prepulse inhibition) disrupted by $5HT_2$ receptor activation. Prepulse inhibition is a phenomenon of sensory gating that is disrupted in schizophrenics and in animals given psychotomimetic agents such as amphetamine and PCP. In rats, prepulse inhibition is disrupted by 5-HT releasing agents or specific $5-HT_2$ agonists, and these effects were attenuated by (+)-α-(2,3-dimethoxyphenyl)-1-[2-(4-fluorophenyl)ethyl]-4-piperidinemethanol (MDL), as described below.

Prepulse Inhibition (PPI)

Test Procedure

After an approximate pretreatment time, rats were placed in the startle chambers for a 5-minute acclimation period. This was followed by 10 minutes testing: 10 trials with an auditory prepulse; 10 trials with a visual prepulse and 10 trials with no prepulse, presented in the same pseudorandom order. The intertrial interval of approximately 20 seconds resulted in a session length of about fifteen minutes, including the five minute acclimation period. PPI was operationally defined as a significant decrease of startle amplitude within a group, following prepulses, compared to its own amplitude in the no prepulse condition.

Stimulus Parameters

The startle eliciting stimulus was a 40 msec of white noise at a sound pressure level of 120 dB. The auditory prepulse stimulus was a 20 msec, 78 dB burst of white noise presented 100 msec prior to eliciting stimulus against a constant 64 dB background of white noise. These parameters were selected to be very similar to those used in most of the studies reviewed in Geyer, M. A., Swerdlow, N. R., Mansbach, R. S., and Braff, D., *Startle models of sensorimotor gating and habituation deficits in schizophrenia. Brain Research Bulletin*, 25, 485–498 (1990).

Cross-modal Prepulse Inhibition

Cross-modal prepulse inhibition by a light-stimulus was included to determine if the reported prepulse effects were limited to the single modality of sound. This visual prepulse was created by turning on three incandescent bulbs in the animal chamber (one mounted on the ceiling and one mounted at each end of the test chamber) 75 msec prior to the onset of the startle stimulus. This visual stimulus produced no humanly perceptible or electronically measurable sound, even when the rather loud 65 dB white masking noise was turned off. The estimated rise time of the light prepulse to a peak of about 175 lux was approximately 25 msec. The resultant interval between peak intensity and startle stimulus corresponds rather well to the 50 msec interstimulus interval (ISI) reported in the literature to be optimal for visual prepulses. Hoffman, H. S., & Ison, J. R., *Reflex modification in the domain of startle: I. Some empirical findings and their implications for how the nervous system processes sensory input. Psychological Review*, 87 (2), 175–189 (1980). The dim, red background illumination in the chambers averaged, 2 lux.

Drugs

MDMA (3,4-methylenedioxymethamphetamine), fenfluramine and (+)DOI (1,4-bromo-2,5-dimethoxyphenyl-2-aminopropane) were dissolved in purified, deionized water and administered intraperitoneally at a dose volume of 1 ml/kg. Equivalent amounts of vehicle (VEH) were used for sham injections. All drugs were given 20 minutes prior to testing.

Apparatus

An apparatus consisting of eight separate stabilimeters measured the amplitude of startle reflexes elicited by acoustic stimulation. See Kehne, J, H., McCloskey, T. C., Taylor, V. L., Black, C. K., Fadayel, G. M. and Schmidt, C. J., *Effects of the Serotonin Releasers 3,4-Methylenedioxymethamphetamine (MDMA 4-Chloroamphetamine (PCA) and Fenfluramine on Acoustic and Tactile Startle Reflexes in Rats, The Journal of Pharmacology and Experimental Therapeutics*, 260 (1), pp. 78–89 (1992) for a detailed discussion. Movement of the platform against a transducer produced a voltage proportional to displacement and is reported as arbitrary units from 0 to 4,095. Each stabilimeter was housed in a ventilated, sound-attenuating chamber illuminated by dim, red-filtered light.

Data Signal Calibration

Output of the transducers was calibrated by use of an audio speaker (Radio Shack #40-1021A woofer) with a weighted cone mounted on a jig that was clamped to the platform in the test cage. This delivered a 10 Hz sine wave signal the same frequency as the startle response in the animal. The average output of all chambers was approximately equal. Due to the fact that an equal number of animals in each group was tested in each chamber, exact equalization of outputs was deemed unnecessary.

Figure 1B:
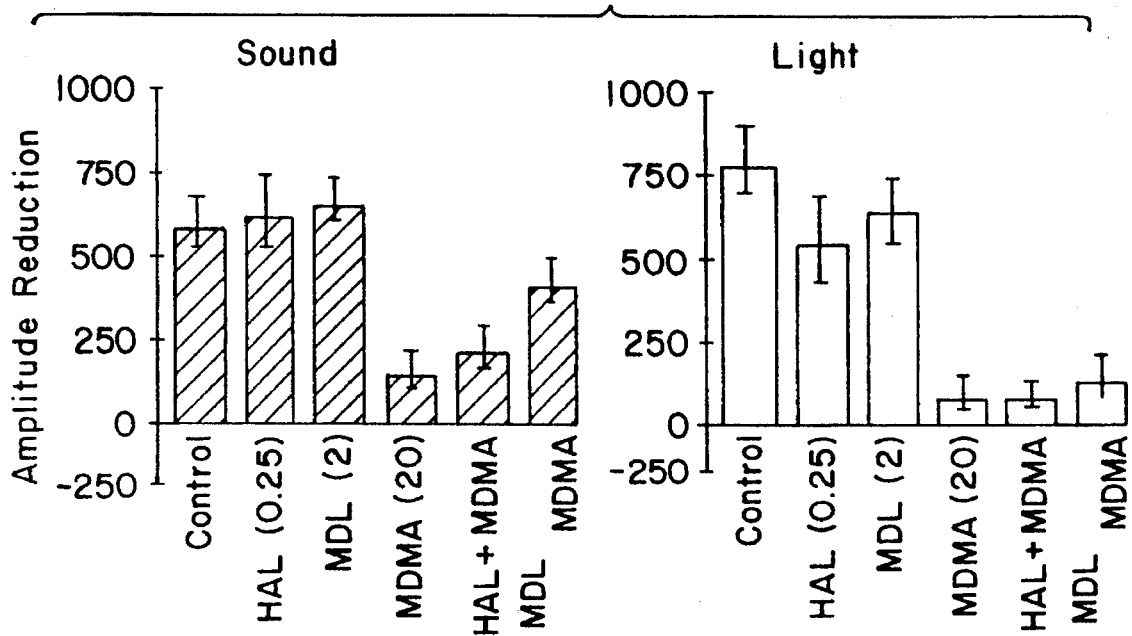

The results from the administration of the drugs in the test procedure described above are summarized in TABLE I presented below. The results of Table I show that MDL attenuates the reduction of prepulse inhibition to sound produced by agents which directly (DOI) or indirectly (MDMA, fenfluramine) stimulate $5-HT_2$ receptors. FIGS. 1a–1b, below, also demonstate that MDL reverses deficits in sensorimotor gating (prepulse inhibition) produced by $5-HT_2$ receptor actvation. (The results in FIGS. 1a–1d also demonstrate that haloperidol, a typical antipsychotic, does not reverse such deficits in prepulse inhibition).

TABLE I

| | PREPULSE INHIBITION TEST RESULTS | | | | | | |
|---|---|---|---|---|---|---|---|
| Treatment | No Prepulse | Sound | Light | Change Sound | Sem | Change Light | Sem |
| VEH + VEH | 1546 | 942 | 743 | 602 | 78 | 803 | 103 |
| VEH + 20 MDMA | 1404 | 1240 | 1310 | 164 | 60 | 94 | 56 |
| 2 MDL + VEH | 1357 | 683 | 704 | 674 | 70 | 653 | 100 |
| 2 MDL + 20 MDMA | 1018 | 585 | 873 | 433 | 72 | 145 | 66 |
| VEH + VEH | 1149 | 831 | 819 | 318 | 57 | 330 | 61 |

TABLE I-continued

| | PREPULSE INHIBITION TEST RESULTS | | | | | | |
|---|---|---|---|---|---|---|---|
| Treatment | No Pre-pulse | Sound | Light | Change Sound | Sem | Change Light | Sem |
| VEH + 5 FENFLURAMINE | 496 | 418 | 426 | 78 | 42 | 70 | 57 |
| 2 MDL + VEH | 909 | 431 | 568 | 478 | 47 | 341 | 72 |
| 2 MDL + 5 FENFLURAMINE | 831 | 340 | 763 | 491 | 72 | 68 | 44 |
| VEH + VEH | 1218 | 723 | 737 | 495 | 73 | 481 | 72 |
| VEH + 2 DOI | 887 | 854 | 494 | 33 | 82 | 393 | 68 |
| 2 MDL + VEH | 1234 | 557 | 754 | 677 | 73 | 480 | 83 |
| 2 MDL + 2 DOI | 837 | 372 | 435 | 465 | 114 | 402 | 102 |

The inhibition of prepulse inhibition was also tested using the compound 2,3-dihydro-N-methyl-1-[4-(trifluoromethyl)phenoxy]-1H-indene-2-methanamine (MDL 2), a selective 5HT uptake blocker.

| Treatment | No Pre-pulse | Sound | Light | Change Sound | Sem | Change Light | Sem |
|---|---|---|---|---|---|---|---|
| VEH + VEH | 1117 | 576 | 681 | 541 | 57 | 436 | 96 |
| VEH + 5 FENFLURAMINE | 678 | 559 | 633 | 119 | 55 | 46 | 60 |
| 5 MDL2 + VEH | 1293 | 819 | 841 | 474 | 62 | 452 | 83 |
| 5 MDL2 + 5 FENFLURAMINE | 767 | 385 | 386 | 382 | 64 | 381 | 77 |

The (+)-isomer of α-(2,3-dimethoxyphenyl)-1-[2-(4-fluorophenyl)ethyl]-4-piperidinemethanol can be prepared by methods known in the art as discussed in European Application No. 0 208 235. One suitable method is disclosed below in Reaction Scheme I:

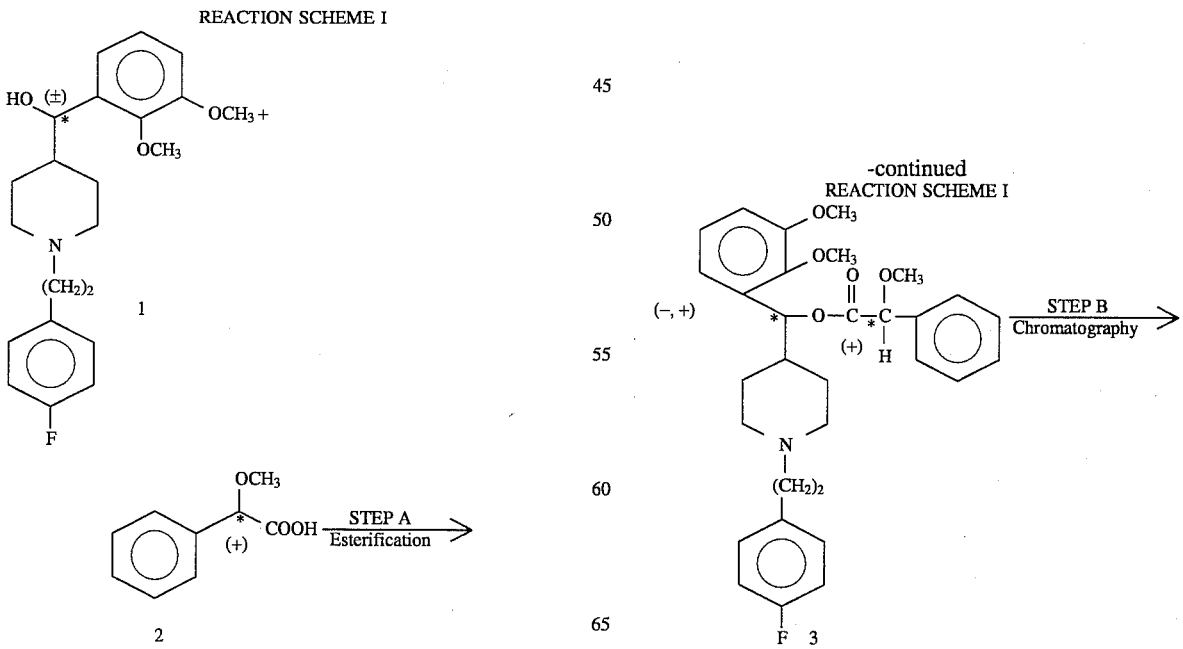

REACTION SCHEME I

-continued
REACTION SCHEME I

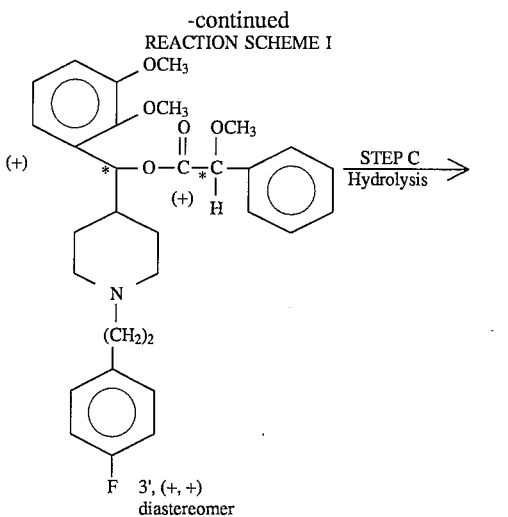

3', (+, +) diastereomer

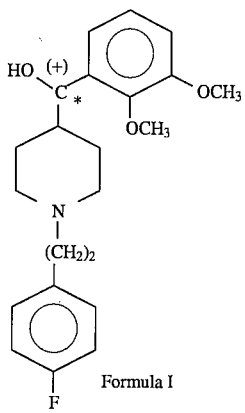

Formula I

In Step A of Reaction Scheme I, an esterification reaction is carried out between racemic α-(2, 3-dimethoxyphenyl)-1-[2-(4-fluorophenyl)ethyl]-4-piperidinemethanol (structure 1) and the (+)-isomer of α-methoxyphenylacetic acid (structure 2). This esterification produces the diastereomeric mixture identified as structure 3. These diastereomers are subjected to silica gel chromatography which separates the two diastereomers, thereby isolating the (+, +) diastereomer as is depicted in Step B. In Step C, the (+, +) diastereomer is hydrolysed which produces the (+)-isomer of α-(2,3-dimethoxyphenyl)-1-[2-(4-fluorophenyl)ethyl]-4-piperidinemethanol.

The esterification reaction can be carried out using techniques known in the art. Typically approximately equivalent amounts of racemic α-(2,3-dimethoxyphenyl)-1-[2-(4-fluorophenyl)ethyl]-4-piperidinemethanol and the (+)-isomer of α-methoxyphenylacetic acid are contacted in an organic solvent such as methylene chloride, THF, chloroform, toluene and heated to reflux for a period of time ranging from 5 to 24 hours. The esterification is typically carried out in the presence of an equivalent amount of dicyclohexylcarbodiimide and a catalytic amount of 4-dimethylaminopyridine. The resulting diastereomers can be isolated by filtration of the dicyclohexylurea and evaporation of the filtrate.

The diastereomers are then subjected to silica gel chromatograpy which separates the (+, +) and the (−, +) diastereomers. This chromatagraphic separation may be carried out as is known in the art. A 1:1 mixture of hexane and ethyl acetate is one suitable eluent.

The resulting (+, +) diastereomer is then subjected to a hydrolysis reaction which produces the (+)-isomer of α-(2, 3-dimethoxyphenyl)-1-[2-(4-fluorophenyl)ethyl]-4-piperidine-methanol. The hydrolysis is carried out by contacting the diastereomer with an excess of a base such as potassium carbonate in an aqueous alcoholic solution. The hydrolysis is carried out at a temperature of about 15° to 30° C. for a period of time ranging from 2 to 24 hours. The resulting (+)-isomer of α-(2,3-dimethoxyphenyl)-1-[2-( 4-fluorophenyl)ethyl]-4-piperidinemethanol may then be recovered by dilution with water and extraction with methylene chloride. It is then purified by recrystallization from a solvent system such as cyclohexane/hexane or ethyl acetate/hexane.

Methods for producing the starting materials of Reaction Scheme I are known in the art. For example, U.S. Pat. No. 4,783,471 teaches how to prepare racemic α-(2, 3-dimethoxyphenyl)-1-[2-(4-fluorophenyl)ethyl]-4-piperidine-methanol. This patent is hereby incorporated by reference. Examples No. 1 and 2 of this application also teach suitable methods. Alternatively, racemic α-(2,3-dimethoxyphenyl)-1-[2-(4-fluorophenyl)ethyl]-4-piperidinemethanol can be prepared in the following manner. Initially 4hydroxypiperidine is subjected to an N-alkylation reaction with p-fluorophenylethyl bromide which produces 4-hydroxy-1-[2-(4-fluorophenyl)ethyl]-piperidine. This compound is brominated with $Ph_3P\cdot Br_2$ which produces 4-bromo-1-[2-(4-fluorophenyl)ethyl]piperidine. This compound is contacted with Mg thereby forming a Grignard Reagent which is then reacted with 2,3-dimethoxybenzaldehyde which produces the desired product (±)-α-(2,3-dimethoxyphenyl)-1-[2-(4-fluorophenyl)ethyl]-4-piperidinemethanol. The (+)-isomer of α-methoxyphenylacetic acid is known in the art.

The dosage range at which (+)-α-(2,3-dimethoxyphenyl)-1[2-(4-fluorophenyl)ethyl]-4-piperidinemethanol exhibits its ability to block the effects of serotonin at the $5HT_2$ receptor can vary depending upon the particular disease or condition being treated and its severity, the patient, other underlying disease states the patient is suffering from, and other medications that may be concurrently administered to the patient. Generally though, with respect to the treatment of OCD, this compound will exhibit its serotonin $HT_2$ antagonist properties at a dosage range of from about 0.001 mg/kg of patient body weight/day to about 100.0 mg/kg of patient body weight/day. The compound is typically administered from 1–4 times daily. Alternatively, it can be administered by continuous infusion. The compounds can be administered orally or parenterally to achieve these effects.

As used in this application:

a) the term "patient" refers to a warm-blooded animal, such as for example rats, mice, dogs, cats, guinea pigs, and primates such as humans;
b) the term "treat" or "treatment" refers to either relieving or alleviating the patient's disease or condition;
c) the expression "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tri-carboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicyclic, 2-phenoxybenzoic, p-toluenesulfonic acid and sulfonic acids such as methanesulfonic acid and 2-hydroxyethanesulfonic acid. Either the mono- or di-acid salts can be formed, and such salts can exist in either a hydrated or substantially anhydrous form. In general, the acid addition salts of these compounds are soluble in water and various hydrophilic organic solvents and which in comparison to their free base forms, generally demonstrate higher melting points; and, d) any reference to (+)-α-(2,3-dimethoxyphenyl)-1-[2-(4-fluorophenyl)ethyl]-4-piperidinemethanol should be construed as encompassing the free base of this compound or an acid addition salt of this compound.

The following Examples are being presented to further illustrate the invention. However, they should not be construed as limiting the invention in any manner.

EXAMPLE 1

Example 1, Steps A–D, demonstrates the preparation of the starting material (±)-α-(2,3-dimethoxyphenyl)-1-[2-(4-fluorophenyl)ethyl]-4-piperidinemethanol according to structure I.

A) 1[2-(4-Fluorophenyl)ethyl]-4-piperidinecarboxamide

A solution of isonipecotamide (10.9 g, 85.0 mmol), 2-(4-fluorophenyl)ethyl bromide (15.7 g, 77.3 mmol), and $K_2CO_3$ (2.3 g, 167 mmol) was prepared in DMF (280 mL) and stirred under argon at 90°–95° C. overnight. The cooled solution was concentrated to a white oily solid. The solid was partitioned between water and $CH_2Cl_2$. The layers were separated and the aqueous layer was extracted with $CH_2Cl_2$. The combined organic layers were washed 2x with water, dried ($MgSO_4$), filtered, and evaporated to a oily solid. The solid was recrystallized from EtOAc to afford 1-[2-(4-fluorophenyl)ethyl]-4-piperidinecarboxamide as a white powder, m.p. 177°–178° C. (decomp.). Anal. Calcd for $C_{14}H_{19}FN_2O$: C, 67.18; H, 7.65; N, 11.19. Found: C, 67.25; H, 7.67; N, 11.13.

B) 4-Cyano-1-[2(4-fluorophenyl)ethyl]piperidine

To stirred phosphorus oxychloride (25 mL, 41.12 g, 268 mmol) and sodium chloride (5.1 g, 87.3 mmol) was added 1-[2-(4-fluorophenyl)ethyl]-4-piperidinecarboxamide (8.9 g, 35.6 mmol) portionwise. After complete addition, the solution was refluxed for 2 hours. The cooled solution was poured into dilute $NH_4OH$ to destroy the $POCl_3$. The aqueous solution was cooled to 0° C., then extracted 2x with $CH_2Cl_2$. The combined organic layers were dried ($MgSO_4$), filtered, and evaporated to afford 8.1 g of an oily solid. The solid was distilled, (b.p. 150° C., 0.1 mm Hg), to afford a clear, colorless oil that solidified. This material was crystallized from hexane to afford 4-cyano-1-[2-(4-fluorophenyl)ethyl]piperidine as white needles, m.p. 47°–48° C. Anal. Calcd for $C_{14}H_{17}FN_2$: C, 72.39; H, 7.38; N, 12.06. Found: C, 72.62; H, 7.49; N, 12.12.

C) 1-[2-(4-Fluorophenyl)ethyl]-4-piperidinecarboxaldehyde

To a stirred solution of 4-cyano-1-[2-(4-fluorophenyl) ethyl]piperidine (1.00 g, 4.3 mmol) in THF (20 mL) under argon at 0° C. was added DIBAL-H (4.6 mL of a 1.0M solution in THF, 4.6 mmol) via syringe. After stirring overnight at room temperature 10% aqueous HCl (25 mL) was added and the solution was stirred for 3 hours. The entire mixture was then poured into 10% aqueous NaOH (50 mL), then extracted 2x with ether. The combined organic layers were washed with brine, dried ($MgSO_4$), filtered, and evaporated to afford a pale yellow oil. The oil was chromatographed on silica gel a eluting with EtOAc. The appropriate fractions were combined and evaporated to afford an oil. This oil was distilled (b.p. 166° C., 0.05 mm Hg) to afford 1-[2-(4-fluorophenyl)ethyl]-4-piperidinecarboxaldehyde, obtained as a colorless oil. Anal. Calcd for $C_{14}H_{18}FNO$: C, 71.46; H, 7.71; N, 5.95. Found: C, 71.08, H, 7.81; N, 5.86.

D) (±)-α-(2,3.Dimethoxyphenyl)-1-[2-(4-fluorophenyl) ethyl]4-piperidinemethanol

To a stirred solution of veratrole (0.93 g, 6.7 mmol) in THF (20 mL) under argon at 0° C. was added n-BuLi (2.7 mL of a 2.5M solution in hexane, 6.75 mmol). After stirring 2.5 h, the solution was cooled to −78° C. and treated with 1-[2-(4-fluorophenyl)ethyl]-4-piperidinecarboxaldehyde (1.30 g, 5.5 mmol) in THF (25 mL) via an addition funnel. The cooling bath was removed and the solution was allowed to stir for 2 hours. Water was added, the layers separated, and the aqueous layer was extracted with EtOAc. The combined organic layers were washed with brine, dried ($MgSO_4$), filtered, and chromatographed on silica gel, eluting with acetone. The appropriate fractions were combined and evaporated to afford a white solid. The solid was recrystallized from hexane to afford racemic α-(2,3-dimethoxyphenyl)-1-[2-(4-fluorophenyl)ethyl]-4-piperidinemethanol as shiny white needles, m.p. 126°–127° C. Anal. Calcd for $C_{22}H_{28}FNO_3$: C, 70.75; H, 7.56; N, 3.75. Found: C, 70.87; H, 7.65; N, 3.68.

EXAMPLE 2

Example 2, Steps A–F, demonstrate an alternative manner of preparing (±)-α-(2,3-dimethoxyphenyl)-1-[2-(4-fluorophenyl)ethyl]-4-piperidinemethanol according to structure I.

A) 1-(1,1-Dimethyethyl)-1,4-piperidinedicarboxylic acid

To isonipecotic acid (107.5 g, 832 mmol) stirred in 1N NaOH (40 g NaOH in 900 mL H2O) and tert-butanol (1800 mL) was added di-tert-butyl dicarbonate (200 g, 916 mmol) in portions. After stirring overnight, the solution was concentrated and the resulting water layer was acidified with aqueous HCl. This acidic aqueous layer was extracted 3x with ether. The combined organic layers were washed with water, brine, dried ($MgSO_4$), filtered, and evaporated to a white solid, which was recrystallized from EtOAc/hexane (300 mL/200 mL) to afford 1-(1,1-dimethylethyl)-1,4-piperidinedicarboxylic acid as white needles, m.p. 147°–149 C.

B) 4-(N-Methoxy-N-methylcarboxamido)-1-piperidinecarboxylic acid 1,1-dimethylethyl ester To a stirred solution of 1-(1,1-dimethylethyl)-1,4-piperidinedicarboxylic acid (50.0 g, 218 mmol) in anhydrous $CH_2Cl_2$ (500 mL) under $N_2$ in a 2 L flask was added 1,1'-carbonyldiimidazole (38.9 g, 240 mmol) portionwise. After stirring for 1 hour, N,O-dimethylhydroxylamine hydrochloride (23.4 g, 240 mmol) was added in one portion. After stirring overnight, the solution was washed twice with 1N HCl , twice with saturated NaHCO3, once with brine, dried ($MgSO_4$), filtered, and evaporated to an oil. Distillation afforded 4-(N-methoxy-N-methylcarboxamido)-1-piperidinecarboxylic acid 1,1-dimethylethyl ester as a clear oil, b.p. 120°–140° C., 0.8 mm.

C) 4-(2,3-Dimethoxybenzoyl)-1-piperidinecarboxylic acid 1,1-dimethylethyl ester n-Butyl lithium (14.5 mL of a 2.5M solution in hexane, 36.3 mmol) was added via syringe to a stirred solution of veratrole (5.00 g, 36.2 mmol) in THF (50 mL, anhydrous) under argon at 0° C. The ice bath was removed and the mixture was allowed to stir for 90 minutes. The mixture was cooled to −78° C. and treated with 4-(N-methoxy-N-methylcarboxamido)-1-piperidinecarboxylic acid 1,1-dimethylethyl ester (9.20 g, 33.8 mmol) in THF (50 mL, anhydrous) via syringe. The cooling dry ice-acetone bath was removed and the mixture was allowed to come to room temperature. After stirring for 3 hours, saturated aqueous NH$_4$Cl was added and the mixture was allowed to stir overnight. The layers were separated and the aqueous layer was extracted with ether. The combined organic layers were washed with brine, dried (MgSO$_4$), filtered, and evaporated to afford an amber oil. The oil was chromatographed on silica gel, eluting with 20% EtOAc in hexane. The appropriate fractions were combined and evaporated to an amber oil. The oil was distilled to afford 4-(2,3-dimethoxybenzoyl)-1-piperidinecarboxylic acid 1,1-dimethylethyl ester as a colorless oil.(b.p. 225°–250° C., 0.05 mm). Anal. Calcd for C$_{19}$H$_{27}$NO$_5$: C, 65.31; H, 7.79; N, 4.01. Found: C, 65.04; H, 7.92; N, 4.11.

D) 4-(2, 3-Dimethoxyphenyl)-4-piperidinylmethanone 4-(2,3-Dimethoxybenzoyl)-1-piperidinecarboxylic acid 1,1-dimethylethyl ester (7.75 g, 22.2 mmol) was dissolved in trifluoroacetic acid (50 mL, 650 mmol) and stirred for 45 minutes. The entire solution was poured into ether (900 mL) and allowed to stand overnight. Filtration yielded 4-(2,3-dimethoxyphenyl)-4-piperidinylmethanone trifluoroacetate as fine white needles, m.p. 123° C. Anal. Calcd for C$_{14}$H$_{19}$NO$_3$.CF$_3$CO$_2$H: C, 52.89; H, 5.55; N, 3.86. Found: C, 52.77; H, 5.62; N, 3.82.

The resulting 4-(2,3-dimethoxyphenyl)-4-piperidinylmethanone trifluoroacetate was dissolved in water, treated with NaOH (10% aqueous) until basic, and extracted three times with dichloromethane. The combined organic layers were washed with brine, dried (MgSO$_4$), filtered, and evaporated to afford 4-(2,3-dimethoxyphenyl)-4-piperidinylmethanone as an oil.

E) (2,3-Dimethoxyphenyl)[1-[2-(4-fluorophenyl)ethyl]-4-piperidinyl]methanone monohydrochloride A solution of 4-(2,3-dimethoxyphenyl)-4-piperidinylmethanone (8.00 g, 32.1 mmol) and 2-(4-fluorophenyl)ethyl bromide (6.52 g, 32.1 mmol) was prepared in DMF (90 mL), treated with K$_2$CO$_3$ (7.0 g, 50.7 mmol), then stirred and heated at 80°C. under argon overnight. The cooled solution was poured into a partition of 2/1 EtOAc/toluene and water. The layers were separated and the aqueous layer was extracted with 2/1 EtOAc/toluene. The combined organic layers were washed 2x with water, 1x with brine, dried (MgSO$_4$), filtered, and evaporated to afford 11.0 g of an oil. The oil was chromatographed on silica gel, eluting with EtOAC. The appropriate fractions were combined, concentrated, dissolved in ethyl acetate and treated with HCl/ethyl acetate. (2,3-dimethoxyphenyl)[1-[2-(4-fluorophenyl)ethyl]-4-piperidinyl]-methanone monohydrochloride was obtained as a precipitate, m.p. 225°–227° C. (decomp). Anal Calcd for C$_{22}$H$_{26}$FNO$_3$.HCl: C, 64.78; H, 6.67; N, 3.43. Found: C, 64.44; H, 6.73; N, 3.41.

F) (±)-α-(2, 3-Dimethoxyphenyl)-1-[2-(4-fluorophenyl)ethyl]-4-piperidinemethanol To a stirred solution of (2,3-dimethoxyphenyl)[1-[2-(4-fluorophenyl)ethyl]-4-piperidinyl]methanone (6.0 g, 16.2 mmol) in MeOH (100 mL) at 0° C. was added NaBH$_4$ (1240 mg, 32.8 mmol) in two portions, over a one hour period. After stirring overnight, the solution was concentrated to a solid. The solid was partitioned between water and ether. The layers were separated and the aqueous layer was extracted with ether. The combined organic layers were washed with brine, dried (MgSO$_4$), filtered, and evaporated to a solid. The solid was chromatographed on silica gel, eluting with acetone. The appropriate fractions were combined and evaporated to afford a white solid. The solid was recrystallized from cyclohexane to afford (±)-α-(2,3-dimethoxyphenyl)-1-[2-(4-fluorophenyl)-ethyl]-4-piperidinemethanol as white needle s, m.p. 126°–127°C. Anal. Calcd for C$_{22}$H$_{28}$FNO$_3$: C, 70.75; H, 7.56; N, 3.75. Found: C, 70.86; H, 7.72; N, 3.93.

EXAMPLE 3

This example demonstrates the preparation of the compound of Formula I.

Preparation of (+)-α-(2,3-Dimethoxyphenyl)-1['-(4-fluorophenyl)ethyl]-4-piperidinemethanol A) Preparation of diastereomers.

A solution of 3.90 g (10.4 mmol) of (±)-α-(2,3-dimethoxyphenyl)-1-[2-(4-fluorophenyl)ethyl]-4-piperidine-methanol, 1.74 g (10.4 mmol) of S-(+)-α-methoxyphenylacetic acid, 2.15 g (10.4 mmol) of 1,3-dicyclohexylcarbodiimide and 0.1 g of 4-dimethylaminopyridine in chloroform (75 ml) was refluxed for 17 hours, allowed to cool to room temperature and filtered. The filtrate was concentrated and chromatographed on a silica gel column eluting with ethyl acetate/hexane (1:1) to afford two diastereomers, Rf=0.1 and 0.2 (TLC EtOAc/hexane, 1:1). Intermediate fractions were rechromatographed to give additional material. Those fractions with Rf=0.2 were combined to give a single diastereomeric ester, (+, +)-(2,3-dimethoxyphenyl)[1-[2-(4-fluorophenyl)ethyl]-4-piperidinyl]methyl-α-methoxybenzeneacetate.

B) Preparation of (+)-α-(2,3Dimethoxyphenyl)-1-[2-(4-fluorophenyl)ethyl]-4-piperidinemethanol To a stirred solution of 0.97 g (1.9 mmol) of the above mentioned diastereomeric ester, Rf=0.2, in 25 ml of methanol was added 0.5 g (3.6 mmol) of potassium carbonate and 5.0 ml of water. After stirring 17 hours at room temperature the reaction mixture was diluted with water and extracted twice with methylene chloride. The combined extracts were washed with water, brine and dried over MgSO$_4$. After filtering, the filtrate was concentrated to an oil and crystalized from 40 ml of cyclohexane/hexane (1:1) to give (+)-α-(2,3-dimethoxyphenyl)-1-[2-(4-fluorophenyl)ethyl]-4-piperidinemethanol, m.p. 112°–113° C., $[\alpha]_D^{20}$=+13.9°.

In order to exhibit these therapeutic properties, the compounds need to be administered in a quantity sufficient to restore prepulse inhibition in a patient having OCD. The dosage range at which these compounds exhibit this effect can vary widely depending upon the severity of the patient's disease, the patient, the particular compound being administered, the route of administration, and the presence of other under lying disease states within the patient, etc. Typically the compounds exhibit their therapeutic effect at a dosage range of from about 0.1 mg/kg/day to about 500 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically a therapeutic amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula (I) can be tableted with conventional tablet bases such as lactose, sucrose, and cornstarch, in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or nonaqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951; 3,797,494; 3,996,934; and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is nonporous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art. The compound can be formulated into pharmaceutical dosage forms using techniques well known in the art.

The compound may be admixed with any inert carrier and utilized in laboratory assays in order to determine the concentration of the compounds within the urine, serum, etc. of the patient as is known in the art.

We claim:

1. A method for the treatment of obsessive-compulsive disorders comprising the administration of a therapeutically effective amount of a 5-$HT_2$ antagonist to a patient in need thereof.

2. A method according to claim 1 wherein the 5-$HT_2$ antagonist is a compound of the formula:

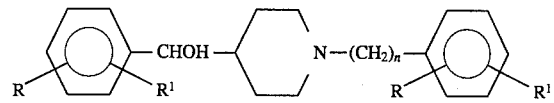

wherein n is 2, 3 or 4 and each R and $R^1$ independently represents hydrogen, $C_{1-6}$ alkyl, halogen, trifluoromethyl, hydroxy, $C_{1-6}$ alkoxy, or amino, their optical isomers and mixtures thereof and the pharmaceutically acceptable salts thereof.

3. A method according to claim 2 wherein the 5-$HT_2$ antagonist is (+)-α-(2,3-dimethoxyphenyl)-1-[2-(4-fluorophenyl)ethyl]-4-piperidinemethanol and the pharmaceutically acceptable acid addition salts thereof.

* * * * *